United States Patent [19]

Cherubini

[11] Patent Number: 5,415,623
[45] Date of Patent: May 16, 1995

[54] POLYMERIC ORTHOTIC DEVICES

[75] Inventor: Julian Cherubini, Newton, Mass.

[73] Assignees: Nicole A. Cherubini; Alexandra Cherubini, both of Newton, Mass.

[21] Appl. No.: 115,939

[22] Filed: Sep. 1, 1993

Related U.S. Application Data

[63] Continuation-in-part of Ser. No. 982,877, Nov. 30, 1992, Pat. No. 5,316,545, which is a continuation of Ser. No. 755,833, Sep. 6, 1991, abandoned.

[51] Int. Cl.$^6$ .............................................. A61F 5/00
[52] U.S. Cl. .......................................... 602/7; 602/20; 602/6; 264/222
[58] Field of Search ........................... 602/6, 7, 20, 21; 482/44, 45; 264/222, 223, DIG. 30; 36/145, 154, 173, DIG. 2

[56] References Cited

U.S. PATENT DOCUMENTS

| | | |
|---|---|---|
| Re. 33,648 | 7/1991 | Brown . |
| 2,457,737 | 12/1948 | Scholl . |
| 3,314,419 | 4/1967 | Quick ........................ 602/7 |
| 3,545,447 | 12/1970 | Silverman . |
| 3,692,023 | 9/1972 | Phillips et al. . |
| 4,240,415 | 12/1980 | Wartman . |
| 4,563,787 | 1/1986 | Drew . |
| 4,669,141 | 6/1987 | Meyer . |
| 4,704,129 | 11/1987 | Massey . |

OTHER PUBLICATIONS

Thermo-Mold Medical Products, Inc. Brochure, 1974.

Primary Examiner—Richard J. Apley
Assistant Examiner—Lynne A. Reichard
Attorney, Agent, or Firm—Wolf, Greenfield & Sacks

[57] ABSTRACT

A preform for use in forming orthotic devices which have a memory in the original preform shape. The preform is preferably formed into a final body shape which retains a memory of the original preform shape.

14 Claims, 5 Drawing Sheets

POLYMERIC ORTHOTIC DEVICES

RELATED APPLICATIONS

This application is a continuation-in-part of U.S. Ser. No. 07/982,877 filed Nov. 30, 1992, now U.S. Pat. No. 5,316,545, which is a continuation of U.S. Ser. No. 07/755,833 filed Sep. 6, 1991 now abandoned. U.S. Ser. Nos. 07/982,877 and 07/755,833 filed Nov. 30, 1992 and filed Sep. 6, 1991 are incorporated by reference herein.

FIELD OF THE INVENTION

The field of this invention is the orthopedic field and the provision of orthotic devices such as heel, ankle and hand supports as well as methods of manufacture of such devices.

BACKGROUND OF THE INVENTION

A wide variety of orthotic devices are known for use in correcting body problems or supporting body structures such as broken or displaced bones, strained or stretched tendons and ligaments or post-surgical repair.

Most orthotic devices which are custom-made of thermoplastic polymeric materials use flat sheets as starting materials. The flat sheets are heated and softened, draped over molds, cooled and hardened, thus forming a finished part. The molds used are generally made from plaster and this requires the taking of plaster impressions from the body part such as an arm or foot region with later formation of a positive mold made from the plaster negative mold.

In some cases, the draping process can be assisted by vacuum forming, pressure forming or other common molding techniques. These products, whether or not formed directly around the body, have a disadvantage in that they produce oversized parts which must be cut to size and then finished, usually in hand operations. The cutting and finishing times can be lengthy and time-consuming.

Conventional plastics used where molds are draped, generally have too high a temperature when moldable to be applied directly to the body and formed.

More recently, in another method of making orthotic devices, low temperature polymeric materials or plastics are used. These plastic materials become malleable at a relatively low temperature as, for example, between 150°-160° F. and can be applied directly to the body so as to obtain the correct body shape while molding. In some cases, flat sheets of such low temperature plastic materials can be pre-cut to reduce the amount of preliminary preparation and secondary finishing.

When complex shapes are made or the amount of forming is large, there is some difficulty. In some cases, the low temperature plastics tend to be thinned in critical areas and in an uncontrolled way. This can weaken and reduce the rigidity of the orthosis in an undesirable way.

Plastics formed by conventional techniques from sheet material also have the tendency to revert to their original shape as, for example, the flat sheet from which they are made. Sometimes a formed orthotic must be reheated and modified. Reversion to the original flat sheet often prohibits such a modification, especially if the original orthotic was trimmed. Such reversion is generally due to the processing characteristics of the plastic. For example, in sheet formation, some stretching and orientation may occur in manufacture and in some cases, if the sheet is anisotropic and subsequently cross-linked, there is a tendency to bring the material back to sheet form under certain conditions of use. Such conditions of use are usually those conditions that exceed normal general use but are present on extremely hot days. Also, should a complete, shaped orthotic be reheated for subsequent modification, it returns to its original flat shape.

SUMMARY OF THE INVENTION

It is an object of this invention to provide a preformed orthotic device which can be shaped to conform to a body configuration and which is provided with a memory so as to maintain that body configuration throughout a variety of conditions of use and which can be re-formed to a variety of variations on the original shape.

Another object of this invention is to provide a means and method in accordance with the preceding objects which can be easily formed from a variety of preforms into a final configuration with minimized cost, finishing requirements, and complexity, yet having a structurally strong and desirable body conformance.

According to the invention, a polymeric orthotic device preform has a memory. The device has a first orthotic shape which is defined by the memory. If the device is heated to a point where the plastic is soft and moldable, it will tend to remain in the orthotic shape. The shape will change only by the affixation of an external force. The polymeric orthotic device preform is capable of being adjusted or stretched and molded into a second orthotic device shape of larger or different dimension or configuration than the first orthotic shape but generally conforming to the overall configuration to the first orthotic shape. Different "configuration" as used in this specification means and includes different size, angular relationships, volume and/or linear dimensions. Thus, an orthotic device can be stretched and formed over the body of a user. Such a formed device can be essentially stable in shape but when subject to extreme conditions of use, will resist being distorted from its conforming shape to the body of the user because of the memory of the device. In a single step by the practitioner, an orthotic device can be custom fitted and biomechanical corrections imparted to it without the need of secondary finishing.

In a preferred embodiment, the polymeric material is a caprolactone polymer which has a molecular weight of about 50,000 and a melting point of about 58°-60° C. with a specific gravity at 20° C. of 1.10 at melt and a viscosity of 1.5 million centerpoise at 100° C.

According to the method of this invention, an orthotic device can be formed by selecting a polymeric material preform comprising a plastic material and having a first orthotic shape and a memory imparted to said preform. The preform is selected to be close in size but smaller or different than a body area to be covered and is generally of a configuration similar to said body area.

The preform is then molded against the body to conform to the body area under conditions such as heating and softening, which retain the memory of the first shape and require some stretching of the material to conform to the body area shape. As the material cools, it reverts to its original mechanical properties; and still retains the memory of the preform, but it holds the shape that it is molded to, so as to conform to the body area.

In some cases, the preform to which the memory has been imparted can be of substantially equal size or larger than the body area which it is to support. Thus, hand or other body splints can have a preform shape having a memory in accordance with this invention, with said shape being larger or smaller than the final shape of the hand with which it is to be used. Thus, the final shape, or final orthotic device, used with the body can be adjusted as desired by heating the preform and reshaping to form a different configuration matching the specific hand, or other body area with which it is used and/or merely changing the preform shape to alter the specific type splint device.

In a preferred embodiment, the orthotic device is a heel cup and ankle support. Such heel cup and ankle supports can be made in three or four standard overall adult sizes and can be of caprolactone polymer. The polymer can be molded to the preformed sizes and then cross-linked to give it a memory such that when heated to soften it from the original shape, it may belstretched from said preformed shape around the body part or mold. If reheated, it will tend to return to said preformed shape at certain conditions of use such as reheating.

In an alternate embodiment of this invention, the orthotic device is a hand splint preform which can be used in the methods of this invention to form final specific orthotic splints and the like. In a preferred embodiment, the hand preform is designed to be useful by being further adjustable to at least two different configurations to treat at least two different common splinting applications. Use of preforms adapted for multiple use can be useful to enable practitioners to carry lower inventories of preforms than otherwise possible.

It is a feature of this invention that the plastic memory imparted to the preform is such that under normal conditions of use, the memory will be unnecessary since the preform when molded to the shape of the body in a final orthotic device, will maintain that molded shape. However, under extreme conditions of use such as at highly elevated ambient temperatures which may occur at times with or without high pressure as in the heel cup use, any change in the shape will be a change tending to return the heel cup to its original smaller shape and thus, tighten and enhance the stability and conformance of the device. More importantly, the memory of the preform is useful if one wants to readjust or remake the final orthotic formed. It is only necessary to heat to obtain the original preform shape, whereupon the preform shape can be reformed or readjusted to any new shape desired.

BRIEF DESCRIPTION OF THE DRAWINGS

The above and other objects, features and advantages of the present invention will be better understood from the following specification when read in conjunction with the accompanying drawings in which.

BRIEF DESCRIPTION OF PREFERRED EMBODIMENTS

Figure 3:
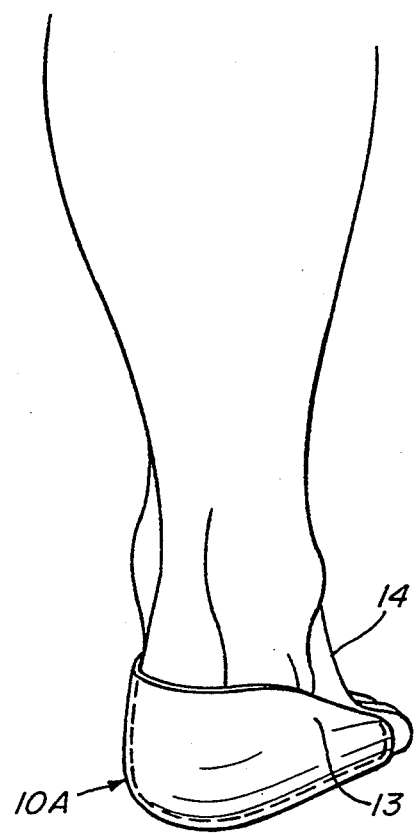
FIG. 3 is a side view of the preform of FIG. 1 after molding into a second shape conforming to the heel and ankle area of a user's foot on the body with which the orthotic device is used.

According to the invention, an orthotic device preform 10 is first formed of a plastic or polymeric material which has or can be processed to have a plastic memory. The preform is illustrated in side view at 10 in the form of a heel cup and ankle support. The heel cup 10 has an upstanding side wall 11 and a bottom 12. The preform 10 is formed into its final shape by molding to a final body configuration of a heel cup, as shown in FIG. 3 at 10A on the foot 14 of a user.

While the preformed orthotic device of this invention is illustrated in this application as a heel cup and ankle support, the preform can be of various shapes and configurations to act as an orthotic device for many uses. For example, the orthotic device preform can be one designed for use with elbows, wrists, knees, ankles or other shapes.

In all cases, the preform 10 is a form closely conforming to the final shape of the orthotic device to be made and of smaller overall therapeutic dimensions than the final device or second shape to be formed from the preform. By therapeutic dimensions, it is meant that where a certain amount of pressure is to be applied to the ankle support or the like, one wants to select a preform that will apply that pressure at the desired area as it may return to its preform shape even though stretched to a second shape during a molding operation. Thus, the device does not loosen but rather will tend to hug and more closely grip the exact contours of the body when it is soft and being molded to the body. An analogy here is a latex rubber glove which is smaller than the hand, but when put on, stretches to fit the exact body. Unlike the glove, preforms will not exert a compressive elastic force when it cools and hardens and will retain the limb configuration if removed from the limb. It should be understood that the preforms of this invention also can be of larger or the same shape as the final orthotic device to be made or used. Thus, the preforms with memory imparted can be used, as is, or stretched to be made smaller, or larger, overall, or to conform and reform limited areas of the preform to certain areas of the body.

The materials useful for the preforms of this invention are any materials which can be provided with a memory in their preform shape. The word "memory" as used in this application is meant to describe the characteristic of memory of plastics or polymeric materials to return to an original shape after distortion from the original state such as molding to a second shape if certain conditions are met, which conditions are usually conditions of a second heating to a heat lower than the melting temperature of the plastic yet high enough to cause deformation of the plastic towards its preform shape. The temperature necessary to activate the memory is generally the same as the second shape molding temperature. The preformed shapes can be imparted memory by various means depending upon the particular plastic or polymeric material used. For example, the memory to return to an original or first shape can be set into that first shape by mechanical forming, chemical radiation or other cross-linking, predetermined stretching, molding in place or other known procedures. In all cases, it is important that when the polymeric material is stretched to a second shape, it has a memory to return to its first shape under extreme conditions of use such as when reheated to temperature at preferably below the temperature, which the preform was formed into the final orthotic device for the user. For example, when a plastic material is formed as a preform and then stretched to exactly meet the contours of the body in a particular application, it will stay in that second shape under ordinary ambient conditions. However, if reheated to modify or change it, the material will tend to shrink back towards and approach its original configuration. Usually this is a temperature-related phenomenon. Reheating enables obtaining the original preform shape which allows reforming to a new or adjusted final orthotic device.

Preferred plastic materials which are capable of having a memory imparted to them include, but are not limited to, caprolactone polymer sometimes known as oxepanone polymer which can be a polymer having the formula

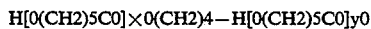

and can contain caprolactone polymer initiated with butane diol. Such polymers are known in the art and are sold under the trade name "Capa 650" by Acquaplast Corporation of Wyckoff, N.J. Such polymers can have molecular weights of about 50,000, melting points of 58°–60° C. with a freezing point of approximately 35° C., flashpoint of 250° C. open cup, specific gravity at 20° C. of 1.10 at melt and viscosity of 1.5 million centerpoise at 100° C. Such polymers are known in the art as "low temperature plastics since they can be reformed or molded at relatively low temperature.

Other polymers known in the orthopedic art and other substitutes therefor which are useful for forming mold-in-place orthopedic and orthotic devices can be used as, for example, noted in U.S. Pat. No. 4,019,505. This patent notes the use of a thermoplastic polyester having a melting point between 40° C. and 70° C. which is a poly(epsilon-caprolactone) polymer having an average molecular weight of over 30,000. Such materials soften at a sufficiently low temperature that they can be formed directly on a patient without undue injury due to scalding or burning. There are quite a few such high polymers which melt or soften at temperatures ranging from 40° C. to 70° C. which can be used for forming orthotics without causing skin damage. In some cases, higher temperatures can be used when the orthotic is to be formed over a protective layer, although it is preferred that the orthotics of this invention are formed directly on the skin from a preform into a second shape. However, the orthotic can be formed over a secondary mold which may be identical to the body or in a desired configuration for use on a specific body part. The orthotic thus can be formed over a body mold which can be the body itself or a mold designed to give a body fit to the orthotic.

Among the materials which melt in the most desired range are poly(ethylene adipate), poly(epsilon-caprolactone), polyvinyl stearate cellulose acetate butyrate, and ethyl cellulose. The first three materials mentioned exhibit true crystalline melting in this temperature range. In the case of cellulose acetate butyrate and ethyl cellulose the phenomenon noted is the so-called glass transition temperature. Poly(propylene oxide) has a crystalline melting temperature of 74° C. This temperature is a little high to be considered for this use, but as is well-known in the art, judicious addition of comonomers to the poly(propylene oxide) will yield a lower melting temperature.

Such materials preferably have high stiffness so that they can be used at thickness ranges of, preferably, from 1/32" to ¼" and provide considerable support to the body with which the orthotic device is used. Thickness up to ½" or higher can be used in some cases. For example, a 1% secant modulus of 50,000 psi at 23° C. is useful. Other known materials of this type can be used in the present invention.

In the preferred embodiment of this invention, where caprolactone polymer materials are used, preform wall thicknesses of from 1/64" to ¼" inch are preferred for normal orthotic purposes. For example, in the case of heel cups, the walls thickness of the preform and resulting second shape orthotic device is preferably in the range of the 1/16" to 3/16" and in the preferred embodiment is about ⅛". The wall thickness can vary in both the preform and final product by small amounts as, for example, by shaping of the preform to form the second shape and final orthotic product. In all cases, the wall thickness and material used is sufficient to provide the orthotic support or correction required with the particular device used.

In normal use, the preform 10 can be formed by any of a number of ways, but preferably is formed by molding to roughly conform to the shape of a body to which it is used. In the case of heel cups, there may be three or more preform sizes used to cover substantially all adult foot sizes with which the orthotic might be used. In an example of FIG. 1, a small size heel cup is formed of caprolactone polymer having a thickness of ⅛", a front-to-back length of 4", a side-to-side outside dimension of 2" at its widest point and a wall height as shown in FIG. 1 of 1½".

The device 10 is made in a simple compression mold consisting of a male and female mold block. Injection molding, vacuum forming, pressure molding, compression molding and other means can be used to make the preform 10 which is to have a memory. In some cases, the preform 10 can be made with a plastic memory of the shape in which it is in although in most cases, the preform will not have a memory at its first stage of treatment. Preferably the preform 10 is molded from a sheet of low temperature plastic stock material of the types described above.

Figure 1:
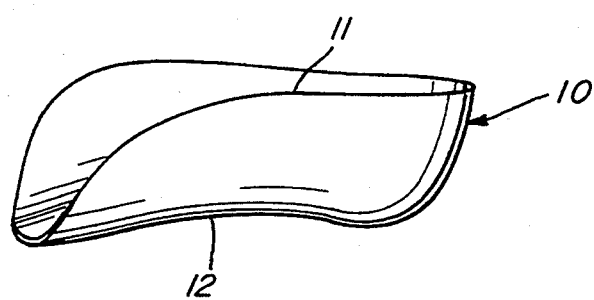
FIG. 1 is a side view of a heel cup and ankle support orthotic device in accordance with the present invention (preform)
Figure 2:
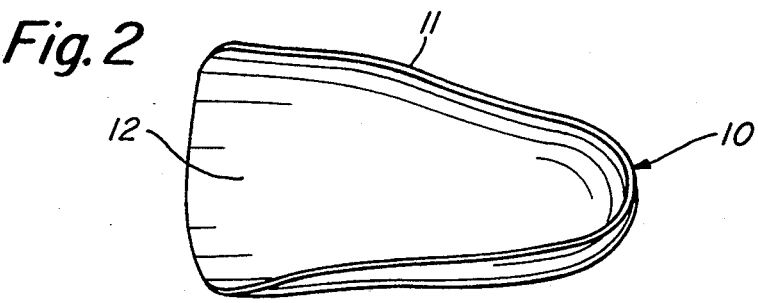
FIG. 2 is a top plan view thereof.

In a second step, the caprolactone preform 10 is cross-linked by radiation so as to impart to it a memory which will cause the material to return (if distended from the preform shape), to the shape as shown in FIG. 1 when temperatures of 140° F. to 200° F. are reached.

In a third step after the cross-linking step, the orthotic device is formed into its second and final shape by stretching the heel cup 10 over the foot of a user to deform the material and stretch it at a temperature of from 140° to 200° F. from its original dimensions by perhaps as little as ¼-inch. Preferably, the degree of stretch is approximately from 1/16 to ½ inch over the field of use. This degree of stretch is kept low by selecting a preform which is slightly smaller in all or part than the body part to which it is to conform in its second shape. In some cases, stretching is to conform to parts of the body and can result in larger, smaller, or the same size configurations.

In the case of the device preform 10, it is fit over a slightly larger heel area of the body stretched to fit at a soften temperature of, for example, 140° to 200° F. This final formation in the second shape can be done by a practitioner such as an orthopedic trained person as by having the heel cup formed over the foot 12 to stretch it to the foot shape, while the heel cup is heated to a temperature in the range of 140° to 200° F.

In ordinary use at ambient temperature, the heel cup remains stiff and substantially unyielding. However, when temperatures exceed 140° F., the heel cup will tend to return to its unstretched form 10, thus conforming more tightly but in an elastic way, to the heel with which it is used. If it is desired to adjust the heel cup after use on the body, this can easily be done by again stretching after softening to a temperature below a temperature which would cause loss of memory. Since the memory is in the preform, as well as the completed original heel cup, the heel cup can be reformed and adjusted in whole or in part as desired. In some uses, the ability to reform as the body heals, and changes in shape are needed, is a significant advantage.

Note that FIG. 3 shows the heel cup 10A conformed to the foot of a user with the ankle support portion 13 shown slightly deformed to an orthotic shape. The second shape of the heel cup in the form 10A is slightly larger then the original shape of the heel cup 10 and has a memory imparted by having cross-linked the preform to bring it back to its smaller dimensions under predetermined conditions such as after stretching if it is reheated.

Note that because the preform is slightly smaller than the heel cup and because the body is merely pressed against the heel cup to deform it to the shape 10A, the practitioner forming the orthotic need not be as highly skilled as one who would form an original shape from a flat sheet or from molded items. The need for specific foot molds is eliminated. The heel cup 10A can be reused and reformed on another foot if desired. There is a timesavings for the practitioner in that a simple series of steps can be used to form a final orthotic product.

No material pre-cutting, pasting, special fit or plastic finishing is necessary in the orthotic devices formed by the present invention.

Positional control of various bones or other body elements can be easily accomplished by conforming the preform to a specific area of the body as the preform stretches or other shape changes can be made with heating so as to automatically obtain desired shapes and supports. For example, if a pressure relief area is desirable, the foot may be spot padded so that subsequent orthotic is formed over the foot and pad.

In all cases, the orthotic second shape is formed by a structurally strong supporting orthoses which provides the desired support to the body.

Figure 4:
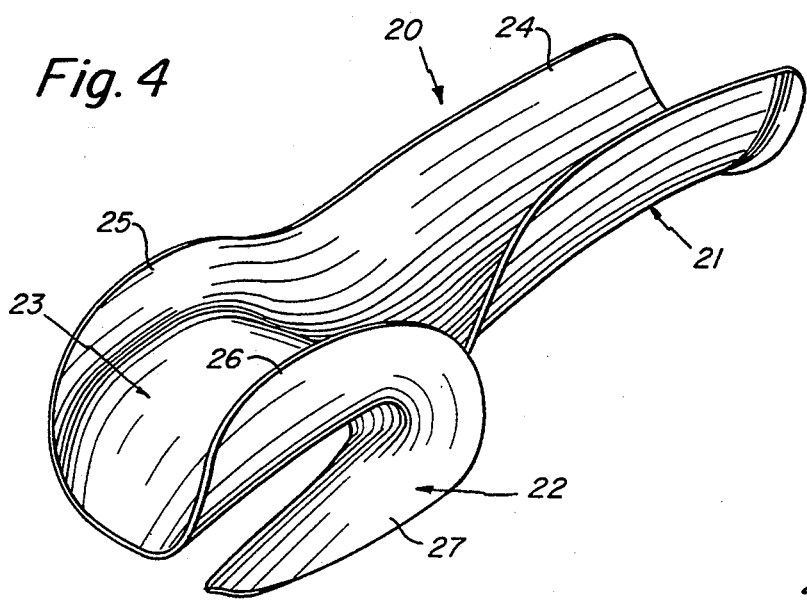
FIG. 4 is a perspective view of a right-hand preform of a hand splint in accordance with this invention.

In another specific embodiment of this invention, a hand splint preform 20 in the shape shown in FIG. 4 is provided as a preform. The preform 20 is in the shape of a functional positional hand splint and can be used to position the thumb with respect to the fingers and the hand with respect to the arm as will be described. The preforms such as 20 are formed into the shape by the methods and procedures used as described with respect to the preform of the heel cup shown in FIG. 1 and have the characteristics and uses the materials as disclosed with respect to the heel cup in FIG. 1 as well as with respect to the orthotic devices of this invention described above. In some cases as for example the specific hand splint preform 20, hand shaping to a mold is the preferred fabrication method.

Figure 8:
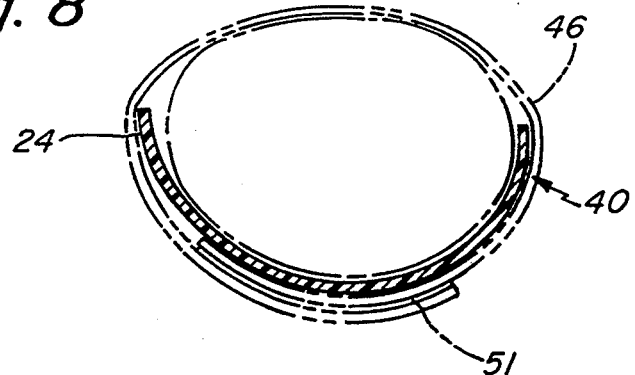
Figure 9:
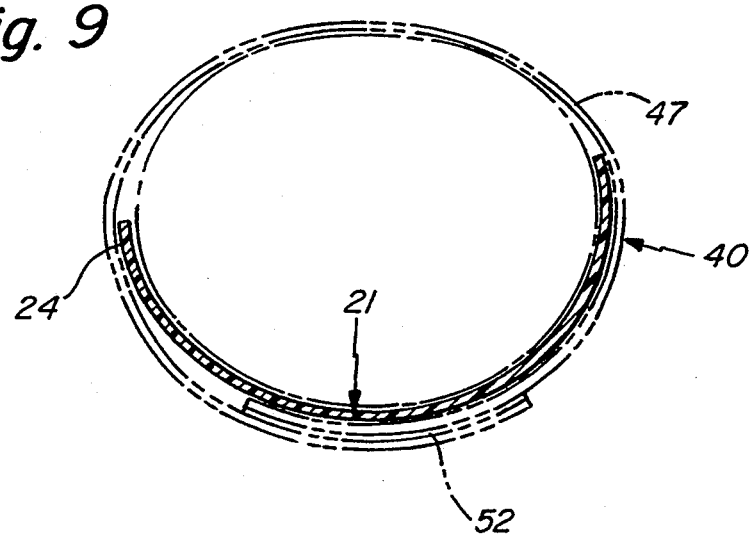
Figure 10:
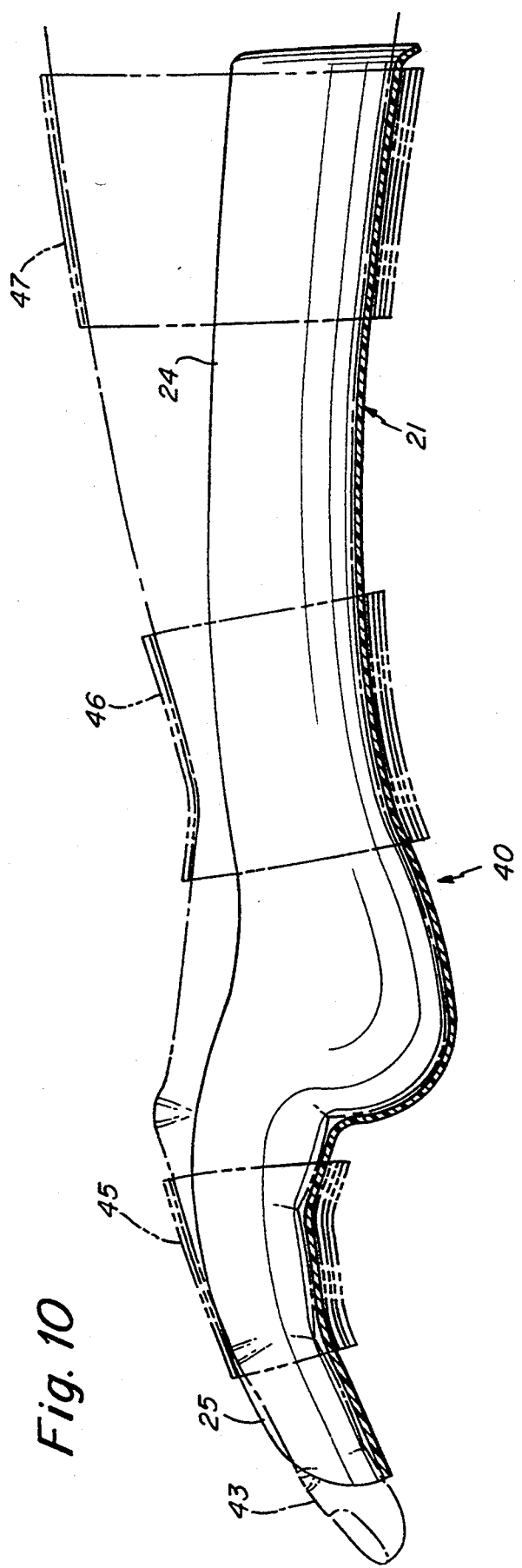
FIG. 10 is a cross-section view taken through line 7—7 of FIG, 7.

Preferably, the preform 20 has a semicircular cross-section elongated arm portion 21, a semicircular cross-section thumb portion 22 and a trough shaped hand positional portion 23. The arm portion 21 is substantially oval shaped as best shown in FIGS. 8 and 9 and has a lip wall 24 extending to form a curved lip hand portion 25 with opposed lip side wall portion 26 which curves downwardly to form a sidewall portion 22 of the thumb portion 27. Thus, the hand and thumb portions 22 are designed to position the hand and thumb of the user with respect to the arm. Note that the splint has a central axis shown in dotted line in FIG. 5 at 30 while the thumb portion has a central axis shown in FIG. 5 at dotted line 31 which intersects with axis 30 at a predetermined angle.

The preform 20 can be the same size, slightly larger or slightly smaller than the hand, wrist and arm with which it is to be used. When in the preform configuration shown in preform 20, the orthotic device of the preform 20 has been given a memory as described above. Preferably, this is carried out by forming the preform from a flat sheet of low temperature plastic into the shape shown in FIG. 4. The preform can be formed by other molding methods as described above with respect to the heel cups preform. After formation and molding by hand to a mold of the shape shown in FIG. 4, the material is given a memory by cross-linking or otherwise.

In the preferred embodiment of the hand splint preform 20, the material is a polycaperlactone-based extruded sheet material obtained from Bixby Corporation, Newburyport, Mass. and sold under the trademark Bixform. The sheet material which can be ⅛" thick is heated to a temperature of 160° F. to form the preform in the shape shown in FIG. 4 having a nominal thickness of ⅛" with reduced areas where stretching occurs). The preform is then irradiated at doses of between 5 to 40 megarads using a cobalt gamma irradiator. Values of about 10 megarads are sufficient to impart sufficient memory to the material whereas below 5 megarads, not sufficient memory was obtained. Above 40 megarads embrittlement was noted with this material. Best results are obtained in the 10-15 megarad range. Of course, it is preferred to minimize the dosage given to the material to avoid higher processing costs. Various forms of irradiation can be used as noted above. For example, electron irradiation can be used and the times and dose rate can change considerably. In all cases, a memory is imparted to the preform 20 so that after formation by a user to conform to a final shape, when reheated, substantially the shape of FIG. 4 will be regained.

The preform 20 has an elongated forearm axis 30 with a thumb axis 31 meeting axis 30 at an angle. When the preform is later shaped to be used, as for example in the shape shown in FIG. 11, the angle of the thumb axis and main forearm axis may change. At the same time the wrist extension or flexion may be changed at the practitioner's direction. In the splint 70, the fingers and thumb are still in the functional position and substantially parallel. That angle can be maintained at the angle of FIG.

Figure 11:
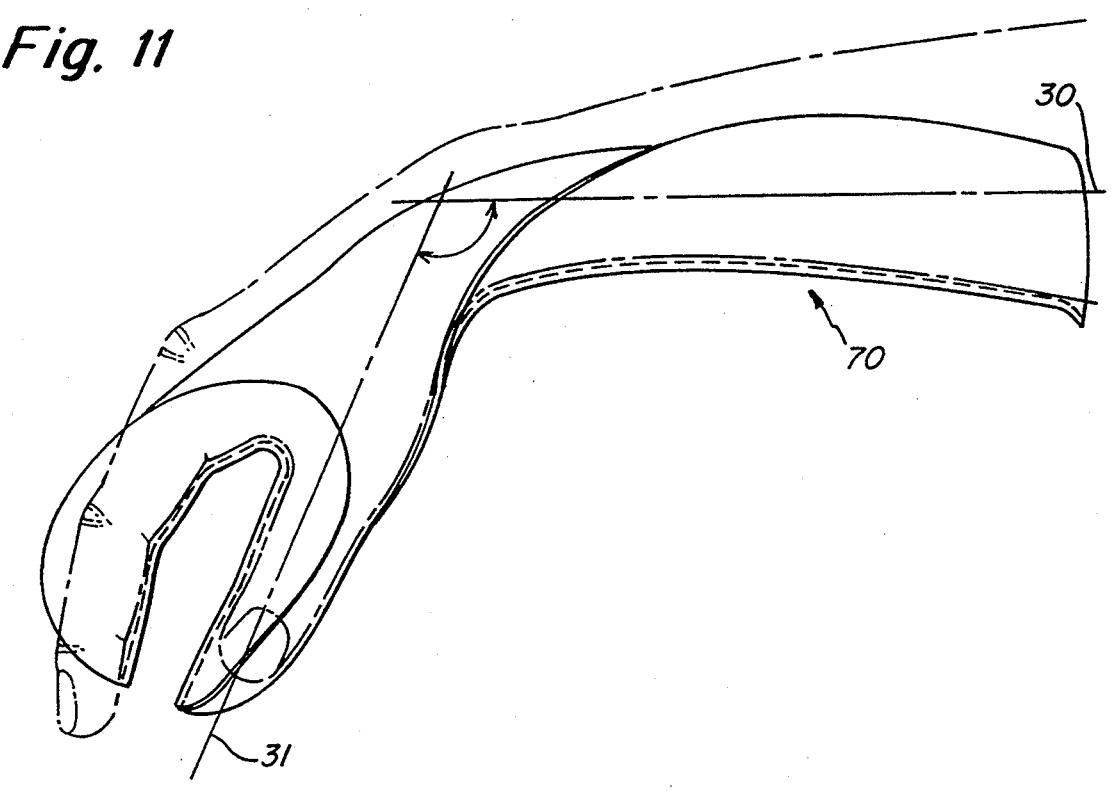
FIG. 11 is another embodiment of a final splint made from the preform shown in FIG. 4 and showing a hand supported by the hand splint of FIG. 11.

5 substantially as the preform was originally designed and can give one type of splint such as a functional resting hand splint. A second type of splint for a second body correction can be made by using the angle shown in FIG. 11. The final splint 70 shown in FIG. 11 is formed from preform 20 by molding to conform to a hand to be positioned at the axis angle between axis 30 and 31 as shown. Such angle can vary and as shown is over 90°.

Figure 5:
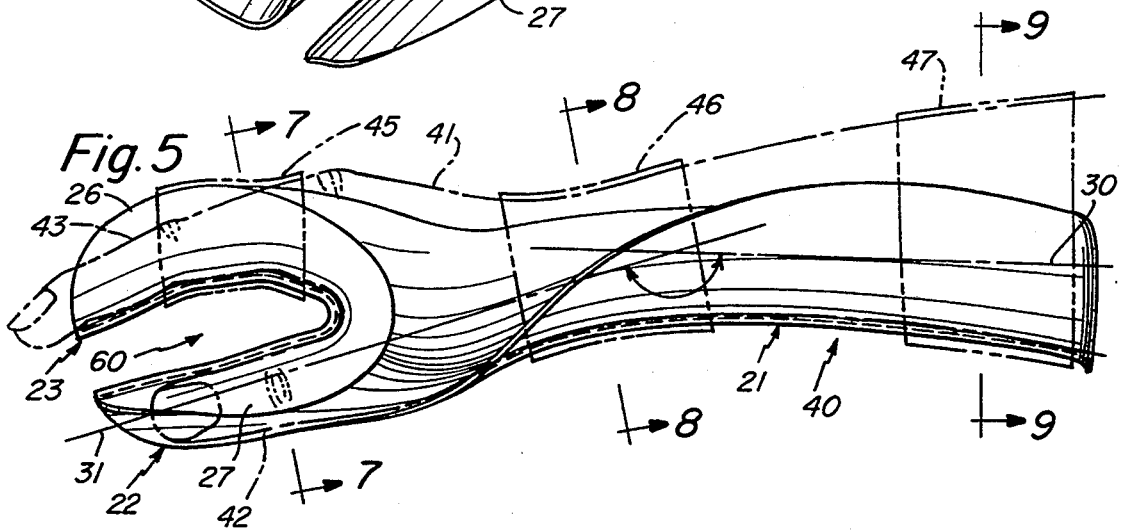
FIG. 5 is a right side view of the preform after it has been formed into a finalized splint by further molding from the shape of FIG. 4 which molding is slight and also includes a hand.and straps shown in dotted outline.
Figure 6:
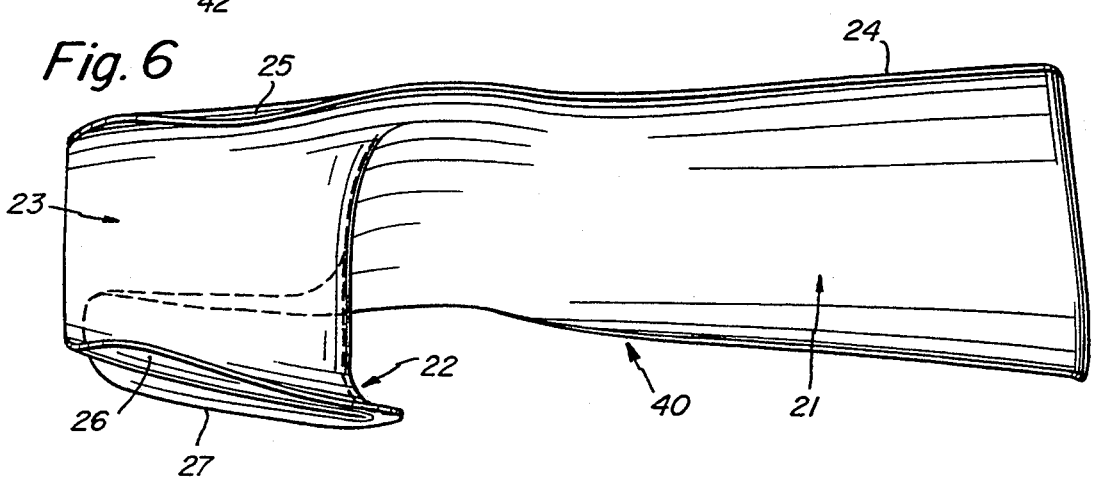
FIG. 6 is a top plan view of the final splint of FIG. 5.

It should be noted that although a human hand is shown in the final splint of FIG. 5, the orthotic devices of this invention can be used for man and other animals such as dogs, cats and horses.

In forming the preform 20 to the final orthotic device or splint 40 shown in FIG. 5, a hand as shown in dotted outline at 41 can be matched to the splint by reformation of the preform 20. This is accomplished in the preferred embodiment by dipping the splint in hot water heated to the molding temperature used to form the preform 20. For example, preform 20 can be immersed in 160° F. water for about 44 seconds enabling it to be reformed to the hand shown in FIG. 5. At this temperature, the hand can be placed in the splint with adjustments made to conform to the individual specific hand and hand positions with which the splint is to be used. Moreover, the splint can be made larger or smaller as desired for the specific hand and can be shaped to change the axis angle relationship between the thumb axis, wrist axis and the main splint axis to form different types of splints as desired. When formed into the device of FIG. 5 shown at 40, the thumb 42 is positioned with respect to the fingers 43 in a predetermined position which can be parallel.

Velcro fasteners (not shown) are used to hold straps or bands 45, 46 and 47 snugly around the hand and arm locating the hand and arm within the final orthotic device 40. Tape such as adhesive tape, cloth bands, plastic bands, buckles on straps and the like can be used for this purpose. The number of straps used is up to the individual user and plays no part of the present invention. In the preferred embodiment, three straps are used to fully secure the hand and maintain it within the orthotic device.

The custom fit to the hand is obtained simply by immersing the splint in the water for about 44 seconds at 160° F. The material selected does not leave fingerprints and it is much easier to conform to the hand being treated than when starting with a flat piece of material. The material is very flexible after the heating process so that when placed on the arm of the user in the normal fitting procedure, the therapist's fingers can easily adjust the preform. The patient's hand can be slid into the still soft preform to form the finger platform to a different dimension of the preform if needed. Total time for fitting the individual can be short in the range of, for example, 4–6 minutes. The material hardens quickly and the final straps or taping can be used to maintain the hand in the splint 40.

It is an important feature of this invention that a single preform such as 20 can be used to form two or more different types of functional splints to service two or more types of defects in hands. Similarly, when other shapes are used for other parts of the body, they too can service more than one defect. This enables therapists to maintain lower inventories since a single preform can be used to treat many different problems. For example, the preform 20 can be used for a stroke victim where it is often desired that the angle between the thumb axis and the main axis 30, or the wrist extension, can vary between 5°–30° at times. The same preform 20 can be used for burn splints where the wrist flextion and thumb portion can be controlled as for example in FIG. 11 where a final orthotic device 40 is formed from preform 20 with a significant angle between the two axis shown. The preform 20 can be used in a resting pan splint where generally 0° extension of the wrist is desired.

In the specific splint 40 shown, its preform 20 can have an overall length of preferably about 12 to 15 inches, an overall thickness of preferably about 0.1 to 0.127 inch and most preferably 0.115 inch with the hand portion being adapted for a normal sized human hand. The preform 20 and final splint 40 are substantially equal in size but have slight variations to account for the specific type of final splint desired and the specific shape of the body portion being supported. The sizes can vary from large, medium, small in accordance with normal glove sizes of small, medium, large as used commonly in the United States.

Figure 7:
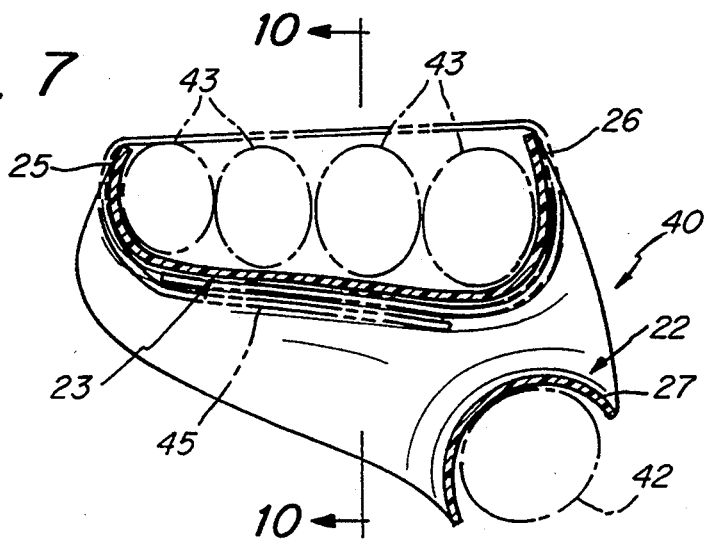
FIGS. 7, 8 and 9 are cross-sectional views of the side view shown in FIG. 5.

FIG. 7 shows a cross-section where the fingers 43 and thumb of the user are nestled within the final orthotic device 40. Device 40 has been enlarged somewhat during final molding of the preform 20 while the thumb portion 42 remains substantially in the preform shape shown.

FIGS. 8 and 9 show a cross-section where the straps 46 and 47 respectively, each have a Velcro fastener 51, 52 respectively to hold the arm portions within the final orthotic device 40.

While specific embodiments have been shown and described, it will be obvious that many modifications are possible and within the scope of this invention.

The hand splint preform 20 and resulting hand splint 40 preferably provide the thumb opposed to the fingers with a U-shaped trough 60 therebetween. The spacing of the thumb from the fingers can be varied as desired in final shaping from the preform shape to the final orthotic device 40 and will vary with the individual being fitted for the final orthotic device.

While low temperature polymeric materials or plastics are preferred for use in this invention, the preforms of this invention can be made from high temperature materials so long as those materials can be given a memory. Thus, as long as a returnable memory can be imparted to the preforms such as 20, later molding can conform the preform into the final orthotic shape by making it larger, smaller or in some cases making only minor modifications if necessary. It is only necessary that the final molding to form the final shape such as 40 from the preform 20 be at such conditions that the memory imparted to the preform will remain in the final shape.

While low temperature plastics are preferred for use, other materials which can be given a memory can also be used. Such other materials include polyethylene and polypropylene.

The fact that the memory of the preform in the shape of the preform remains, allows one to readjust splints and orthotic devices at any time by further molding. In addition, the splints can be reused as necessary since the shape of the preform can be obtained by reheating to the softening temperature. More often, as the progress of a particular disease proceeds, it may be desirable to make adjustments in a particular splint to accommodate changes or improvement in the user of the splint. Thus, a user can bring the splint back to the therapist and the therapist can reform it for that same user by minor adjustment or major adjustment as may be necessary.

What is claimed is:

1. A preform polymeric orthotic device having a memory imparted by a processing step, said device having a first three dimensional orthotic shape defined by said memory which memory is capable of bringing said device to said orthotic shape at a predetermined temperature, said polymeric orthotic device being capable of being softened and subsequently being molded into a second orthotic shape of different dimension than said first orthotic shape without destroying said memory, but closely conforming in overall configuration to said first orthotic shape, whereby an orthotic device can be formed into said second orthotic shape over a body mold and can be essentially stable in shape while being capable of being brought back to said preform shape.

2. A preform polymeric orthotic device in accordance with claim 1, wherein said orthotic device is adjusted to said second shape and has a memory tending to bring said device to said first orthotic shape if reheated to a predetermined temperature, said preform being itself formed from a flat sheet of polymeric material.

3. A preform orthotic device in accordance with claim 2, wherein said device is formed of a low temperature plastic and stretching is carried out to mold into said second orthotic shape at elevated temperature below the melting point of said plastic and at the stretching temperature of said orthotic device.

4. A preform polymeric orthotic device in accordance with claim 3, wherein said device is formed into a heel cup.

5. A preform orthotic device in accordance with claim 1, wherein said device is formed of caprolactone polymer capable of being processed to have a memory at said predetermined temperature.

6. A preform polymeric orthotic device in accordance with claim 1, wherein said device is crosslinked and later stretched to conform to a shape which acts as an orthotic shape.

7. A preform in accordance with the preform of claim 1 wherein said preform polymeric orthotic device is in the shape of a hand splint.

8. A preform in accordance with the preform of claim 7 wherein said preform is constructed and arranged to be designed for final molding to at least two different positions to treat at least two different conditions of the hand.

9. A preform in accordance with the preform of claim 8 wherein said preform is formed of a low temperature polymeric material.

10. An orthotic device having a final orthotic shape conforming to a body part of an individual, said device having a memory for returning said device to a three dimensional orthotic shape other than said final orthotic shape, but closely conforming thereto, and said device being formed of a low temperature polymeric material and said memory is imparted by cross linking.

11. An orthotic device in accordance with claim 10 wherein said device is formed of a low temperature polymeric material having been first formed into a sheet material having at thickness from 1/32 inch to ½ inch and then molded into a preform which is then processed to impart a memory at a first temperature, said orthotic device being formable to conform to the body of a user at a temperature below that which would cause loss of memory from the memory imparted to said preform.

12. An orthotic device in accordance with claim 10 wherein said device is in the form of a hand splint having an arm section, a finger section and a thumb section.

13. An orthotic device in accordance with claim 12 wherein said hand section has been modified by heating to obtain a final shape but maintaining a memory in a preform shape.

14. An irradiated preform polymeric orthotic device having a memory, said device having a first three dimensional orthotic shape defined by said memory which memory is imparted by a separate processing step by irradiation, said polymeric orthotic device being capable of being softened and subsequently being molded into a second orthotic shape of different configuration than said first orthotic shape, but closely conforming in overall configuration to said first orthotic shape, whereby an orthotic device can be formed into said second orthotic shape over a body mold and can be essentially stable in shape, conforming to the body of a user.

* * * * *